(12) United States Patent
Lee

(10) Patent No.: US 7,322,985 B2
(45) Date of Patent: Jan. 29, 2008

(54) SURGICAL SAW FOR CUTTING OFF CHEEK BONES

(76) Inventor: Jae Hwa Lee, 4F. 1306-8 Seocho-dong, Seocho-gu, Seoul, 137-070 (KR)

( * ) Notice: Subject to any disclaimer, the term of this patent is extended or adjusted under 35 U.S.C. 154(b) by 604 days.

(21) Appl. No.: 10/399,270

(22) PCT Filed: Sep. 6, 2001

(86) PCT No.: PCT/KR01/01504

§ 371 (c)(1),
(2), (4) Date: Apr. 16, 2003

(87) PCT Pub. No.: WO02/36023

PCT Pub. Date: May 10, 2002

(65) Prior Publication Data

US 2004/0024405 A1 Feb. 5, 2004

(30) Foreign Application Priority Data

Oct. 30, 2000 (KR) .............................. 2000-64021

(51) Int. Cl.
*A61B 17/56* (2006.01)
(52) U.S. Cl. .................................................. 606/71
(58) Field of Classification Search ................ 606/82, 606/167, 176, 171; 600/564; 83/858, 699.2; 30/304, 506, 166.3, 392, 394
See application file for complete search history.

(56) References Cited

U.S. PATENT DOCUMENTS

| 2,234,242 | A | * | 3/1941 | Gilbert ........................ 30/169 |
| 2,396,443 | A | * | 3/1946 | Singer ......................... 30/304 |
| 2,669,267 | A | * | 2/1954 | Miller ........................ 30/503.5 |
| 3,045,348 | A | * | 7/1962 | Dungan ....................... 30/304 |
| 3,488,843 | A | * | 1/1970 | Tims, Jr. ...................... 30/162 |
| 4,036,236 | A | | 7/1977 | Rhodes, Jr. .................. 128/317 |
| H000571 | H | * | 2/1989 | Hollinger et al. ............. 606/82 |
| 5,423,825 | A | * | 6/1995 | Levine ......................... 606/86 |
| 5,586,842 | A | * | 12/1996 | Bae et al. ................. 407/29.14 |
| 5,846,244 | A | | 12/1998 | Cripe ........................... 606/82 |
| 6,007,541 | A | | 12/1999 | Scott ............................ 606/82 |
| 6,887,250 | B1 | * | 5/2005 | Dority et al. ............... 606/132 |

FOREIGN PATENT DOCUMENTS

EP 0517529 A2 6/1992

* cited by examiner

*Primary Examiner*—Anhtuan T. Nguyen
*Assistant Examiner*—Tuan V. Nguyen
(74) *Attorney, Agent, or Firm*—Ladas & Parry LLP

(57) ABSTRACT

The surgical saw according to the present invention comprises an arm fixed by mounting the rear end portion thereof in a jaw of a handle; and a double saw blade part connected with the front end portion of the arm and having two saw blades arranged side by side in a certain distance. In case that the surgical saw is used in surgeries for cutting off cheek bones, the surgical saw can precisely cut off portions of the cheek bones in a width set in advance by precisely cutting off two positions of the cheek bones in a precise cutting-off length at the same time so that the portions of cheek bones can be conveniently cut off, the periods of time for surgeries can be reduced, and an occurrence frequency of surgery aftereffects due to different cutting-off widths for the left and right cheek bones can be reduced.

3 Claims, 5 Drawing Sheets

SURGICAL SAW FOR CUTTING OFF CHEEK BONES

TECHNICAL FIELD

The present invention relates to a surgical saw for cutting off cheek bones which is used for cutting off portions of cheek bones during plastic surgeries for smoothing bulged cheek bones, and more particularly to a surgical saw for cutting off cheek bones which has spacing-adjustable double saw blades capable of precisely cutting off cheek bones at one time in a predetermined width.

BACKGROUND ART

The cheek bones such as the zygomatic buttresses, are bones bulged out below the tails of the eyes on the both sides of a face. Appropriate cheek bone bulges give a vigorous and good look and a three-dimensional effect, but excessive cheek bone bulges cause a face to look wide and a nose to look relatively low in front view so that the bulges may be a factor for a face appearance to be deteriorated. Particularly, the excessive bulges together with a square chin which is distinctly protruded and angled cause a strong and rough appearance so that they give an adverse feeling to others.

Accordingly, plastic surgeries are being widely carried out to look mild in appearance by smoothing bulged cheek bones in recent.

Methods and difficulty degrees of plastic surgeries for smoothing cheek bones are dependent upon bulged directions and degrees of the cheek bones. In case that cheek bones are protruded forwards, it is enough for their smoothing only to trim off protruded portions of the cheek bones, but in case that cheek bones are severely protruded forwards or cheek bones are protruded sideways, an effect can be brought only when portions of the cheek bones are cut off, and remaining separate portions on both sides are pushed toward each other in order for both cross-sectioned ends of the remaining cheek bones to be joined to each other.

In the meantime, a conventional surgical saw 10 for cutting off cheek bones which is used for removing portions of the cheek bones in cheek bone plastic surgeries has an arm 11 formed in an elongate straight bar shape and a saw portion 12 mounted on the front portion of the arm 11 as shown in FIG. 1, and a fixture portion 11a on the rear side of the arm 11 is mounted in a jaw 21 of a handle 20 in which an electric motor is built, so that the jaw 21 reciprocates the saw to cut off portions of cheek bones 101 of a skull 100 exposed through skin opened by the saw portion 12 as shown in FIG. 2.

However, in case that the conventional surgical saw for cutting off cheek bones as mentioned above is used, the saw portion 12 has only one saw blade so that at least two times cutting operations are needed to partially cut off cheek bones, as shown in FIG. 3, causing a problem that surgeries become very cumbersome as well as require lots of time. Further, a cutting interval has to be adjusted based on naked eyes through the skin opened by cutting, so that it is very difficult to adjust cutting-off widths of both individual cheek bones of a face due to a difficult securing of a visual field, causing a high occurrence frequency of surgery aftereffects bringing an asymmetry of the left and right sides of a face.

DISCLOSURE OF INVENTION

Accordingly, in order to solve the above problems caused by the conventional surgical saw for cutting off cheek bones, it is an object of the present invention to provide a surgical saw for cutting off cheek bones which has two saw blades a distance between which can be adjusted and fixed beforehand to precisely cut off portions of the cheek bones in a predetermined width with a one-time cutting operation.

In order to achieve the above object, the surgical saw for cutting off cheek bones according to the present invention comprises an arm fixed by mounting the rear end portion thereof in a jaw of a handle; and a double saw blade part connected with the front end portion of the arm and having two saw blades arranged side by side in a certain distance.

In the above structure, the individual saw blades of the double saw blade part are preferably fixed on both sides of the front end portion of the arm by a fixing means in a distance to each other.

Further included are at least one or more spacing members selectively placed between the individual saw blades of the double saw blade part and the sides of the front end portion of the arm on which the individual saw blades are closely fixed, and for enabling the distance of the individual saw blades to be adjusted.

Further, the left and right sides of the spacing members and the both sides of the front end portion of the arm, which are closely contacted with each other, have up-and-down movement preventing structures for preventing the individual saw blades from relative rotations with respect to the arm by restraining relative movements in up-and-down directions with respect to each other and movements in up and down directions of the individual saw blades.

Furthermore, the fixing unit includes a bolt transversely penetrating the individual saw blades and the front end portion of the arm and a nut engaged with the bolt.

BRIEF DESCRIPTION OF THE DRAWINGS

The above object and other advantages of the present invention will become more apparent by describing in detail a preferred embodiment thereof with reference to the attached drawings, in which.

BEST MODE FOR CARRYING OUT THE INVENTION

Hereinafter, the structure and operations of a surgical saw for cutting off cheek bones will be described in detail through preferred embodiments of the present invention.

Figure 1:
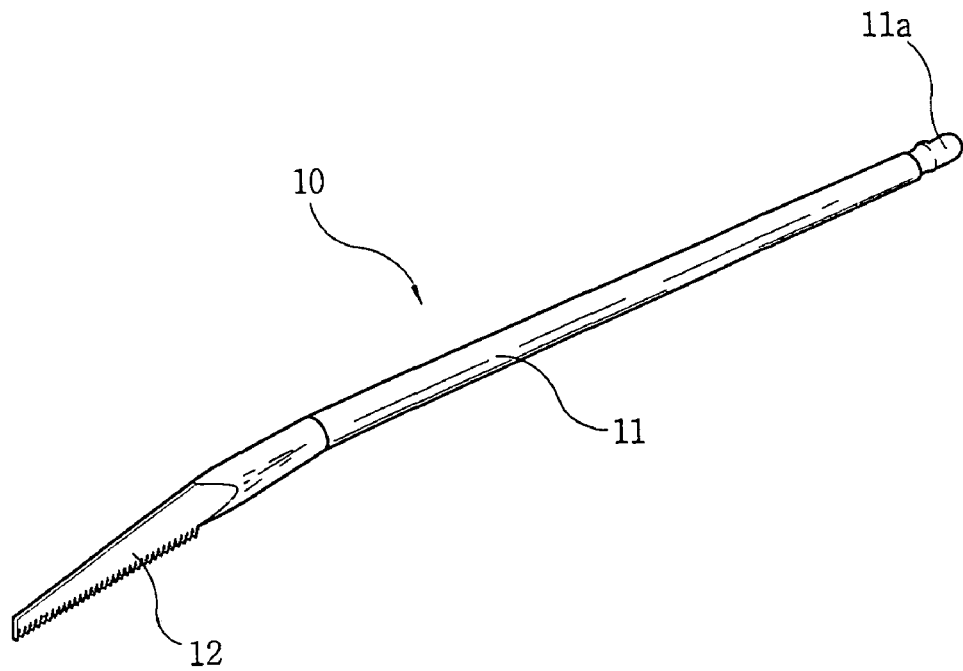
FIG. 1 is a perspective view for showing a conventional surgical saw for cutting off cheek bones.
Figure 2:
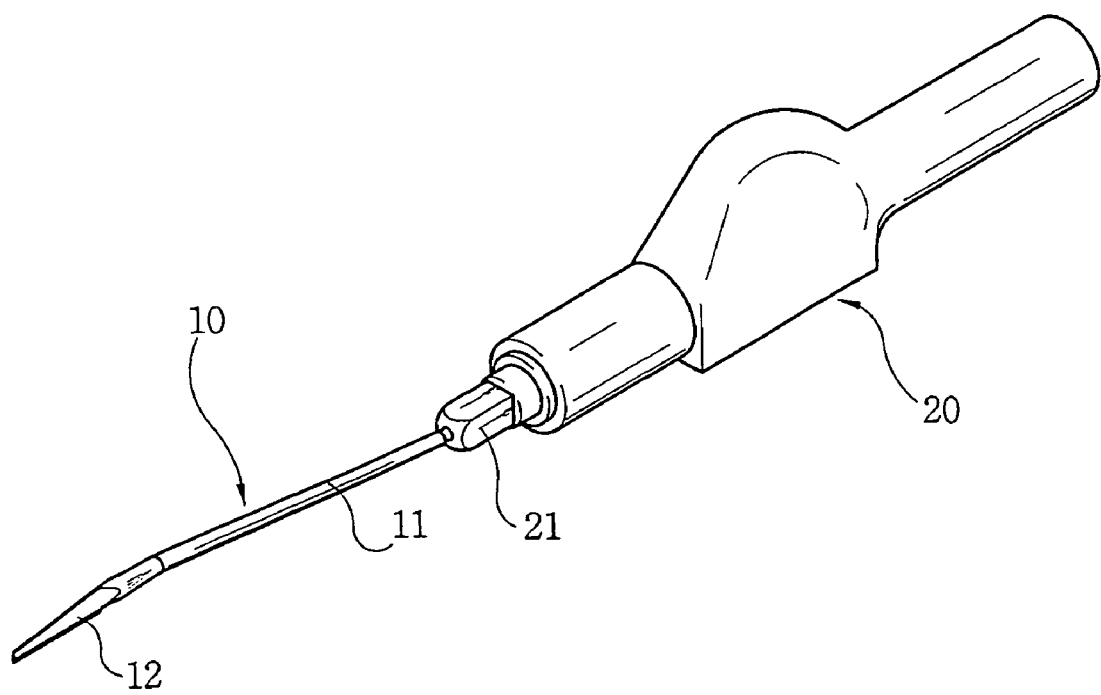
FIG. 2 is a perspective view for showing a motor-driven surgical saw to which a conventional saw for cutting off cheek bones is mounted.
Figure 3:
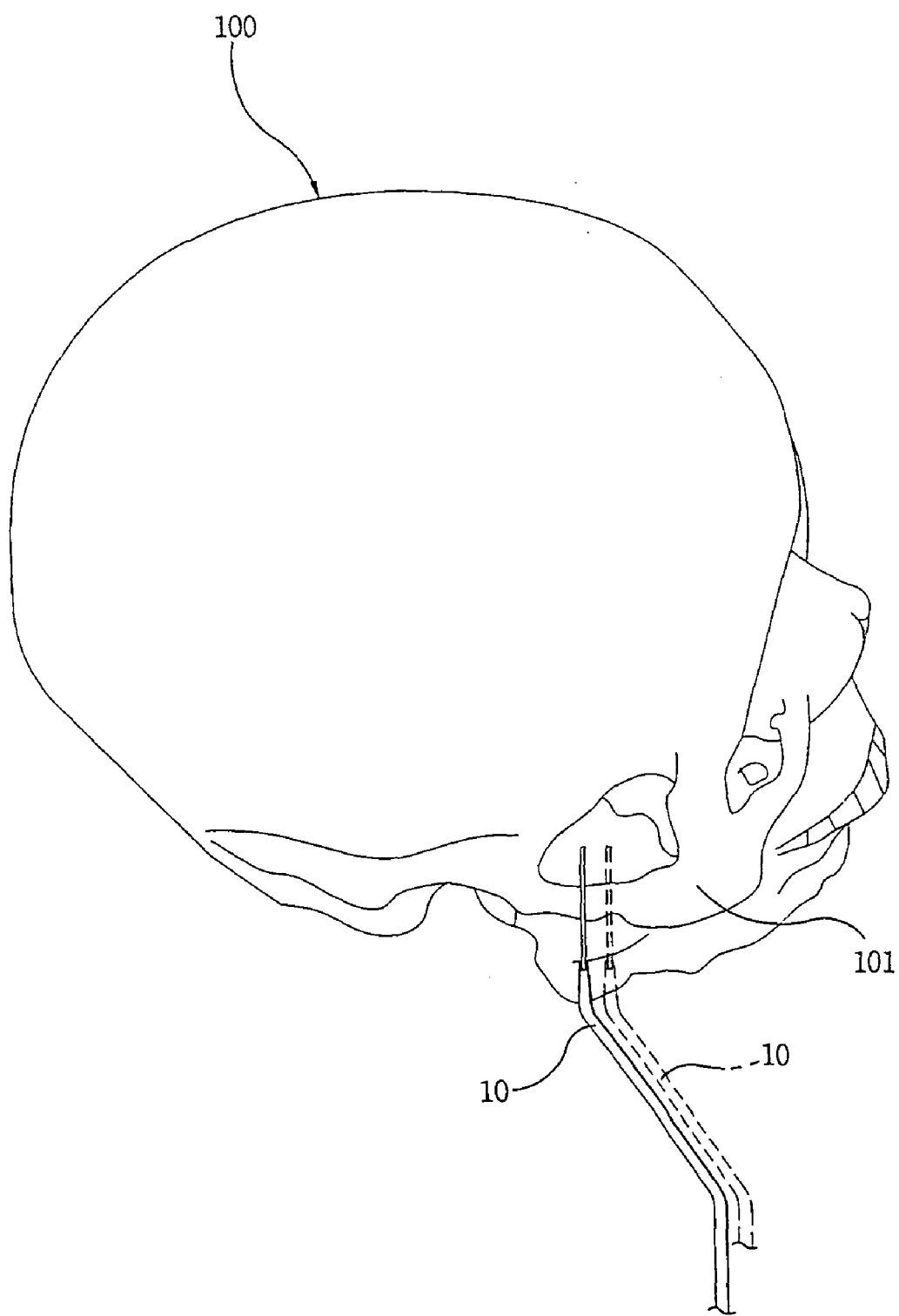
FIG. 3 is a view for showing a conventional surgical saw for cutting off cheek bones in use.
Figure 4:
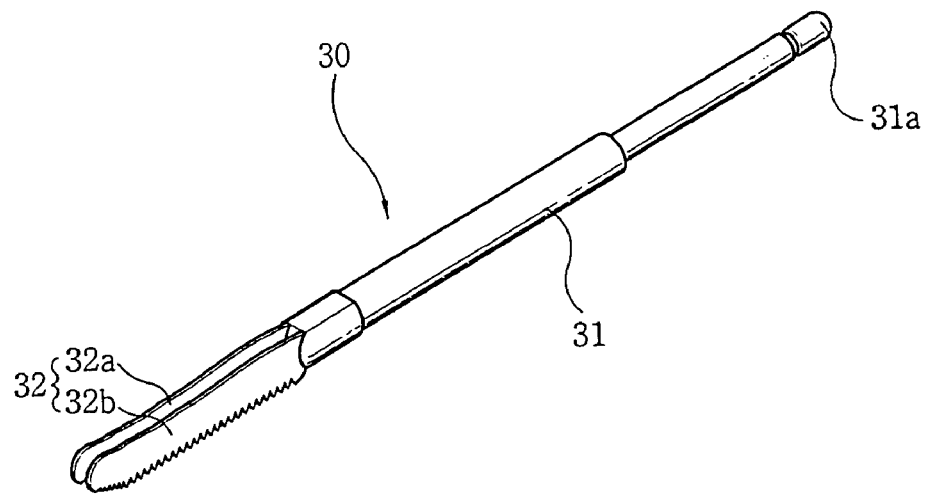
FIG. 4 is a perspective view for showing a surgical saw for cutting lo off cheek bones according to an embodiment of the present invention.
Figure 5:
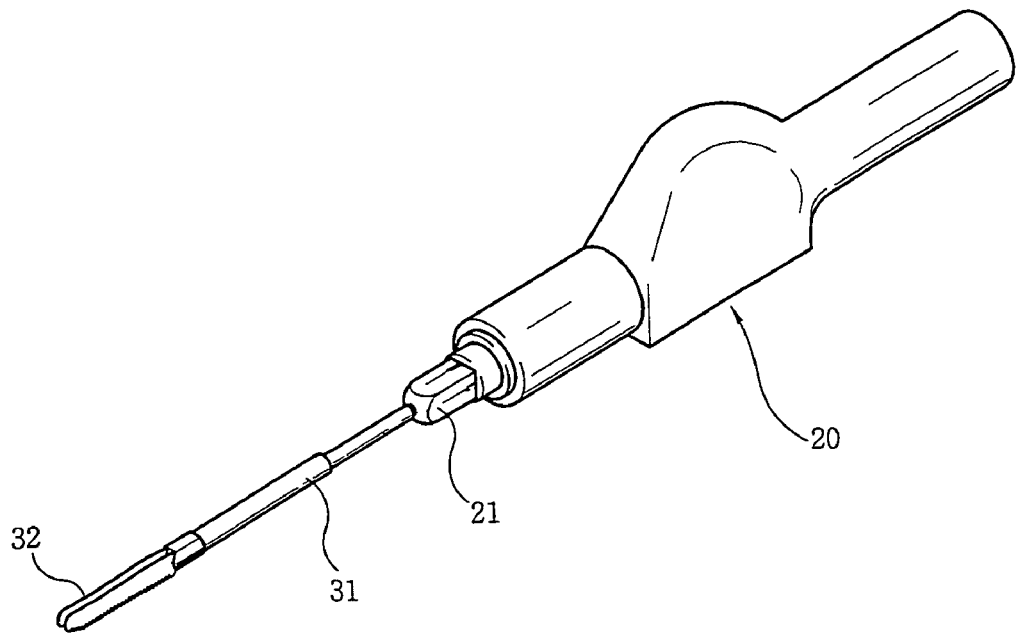
FIG. 5 is a perspective view for showing a motor-driven surgical saw to which a surgical saw for cutting off cheek bones is mounted according to an embodiment of the present invention.

FIG. 4 is a perspective view for a surgical saw for cutting off cheek bones according to an embodiment of the present invention, and FIG. 5 is a perspective view for a motor-driven surgical saw to which a surgical saw for cutting off cheek bones is mounted according to an embodiment of the present invention.

As shown in FIG. 4, a surgical saw 30 for cutting off cheek bones according to an embodiment of the present invention has an arm 31 of an elongate bar shape and a double saw blade part 32 mounted on the front end of the arm 31.

The arm 31 is a round bar of a certain length on the front end of which the double saw blade part 32 is mounted and on the rear end of which a fixture portion 31a having a connection structure is formed to be connected with a jaw 21 of a handle 20, as shown in FIG. 5, so that the double saw blade part 32 is fixed to the handle 20 with a certain distance from the front end of the handle 20 to be easily controlled as well as to transfer a linear reciprocation kinetic energy of the handle 20 to the double saw blade part 32. Particularly, in case that the handle has a motor(not shown) therein as in the present embodiment, a linear reciprocation kinetic energy of the jaw 21 structured to be reciprocated by the motor is transferred to the double saw blade part 32.

The double saw blade part 32 are connected to the front end of the arm 31 to be linearly reciprocated together with the arm 31 so that the double saw blade part 32 directly cut off portions of cheek bones with plural saw teeth formed along the lower sides of the blade part 32. The double saw blade part 32 is constructed with two saw blades 32a and 32b arranged side by side in a certain interval and simultaneously cuts off at least two portions of cheek bones.

Figure 6:
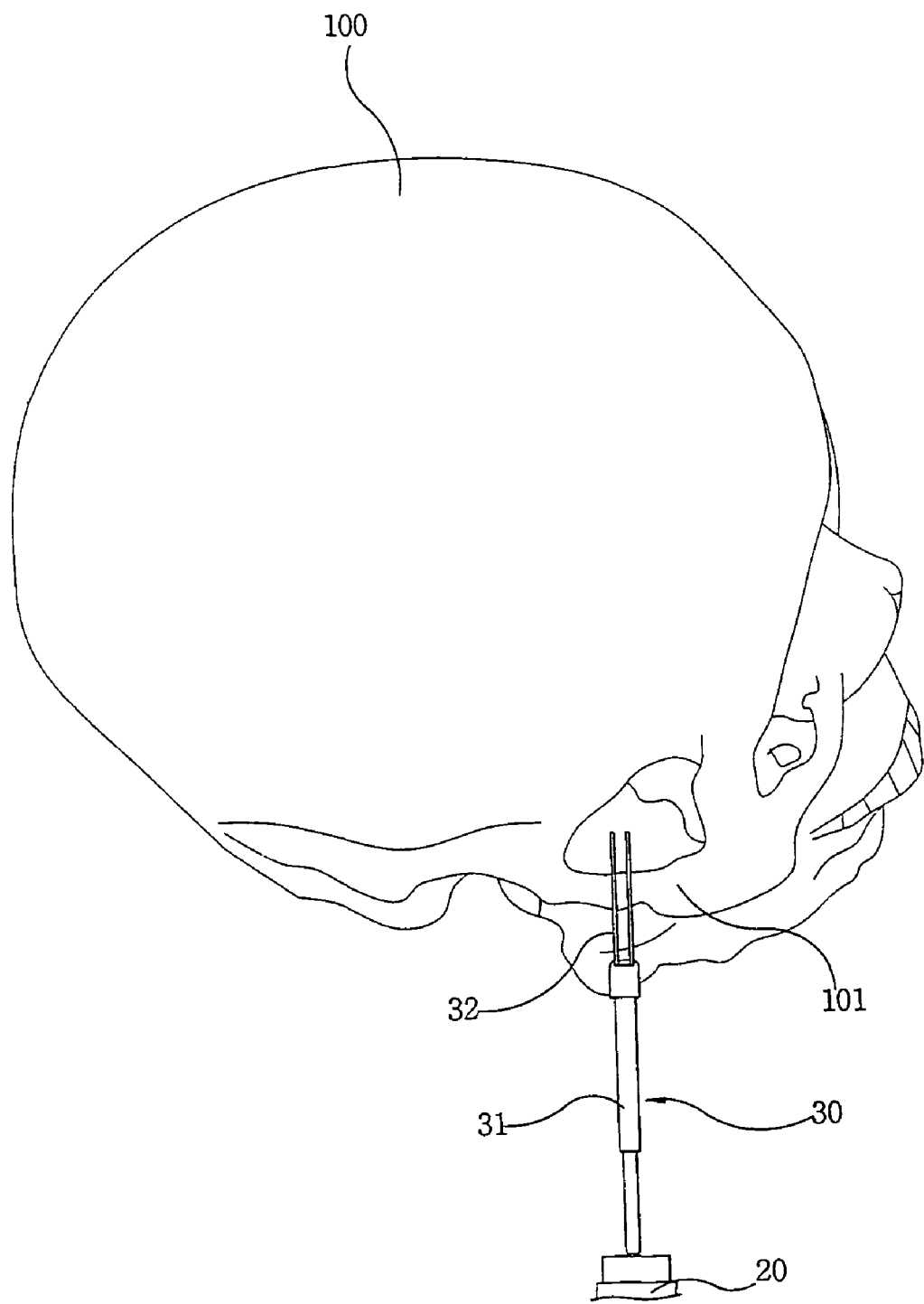
FIG. 6 is a view for showing a surgical saw for cutting off cheek bones in use according to an embodiment of the present invention.

With the above structure, in the surgical saw 30 for cutting off cheek bones according to an embodiment of the present invention, the arm 31 and double saw blade part 32 are linearly reciprocated by the jaw 21 which is linearly reciprocated by the motor built in the handle 20, and, in case that the surgical saw 30 is used in surgeries for cutting off portions of cheek bones as shown in FIG. 6, the surgical saw 30 can saw at least two positions of cheek bones 101 at the same time so that the saw 30 can cut off a portion of the cheek bones 101 with only a one-time cutting operation.

Figure 7:
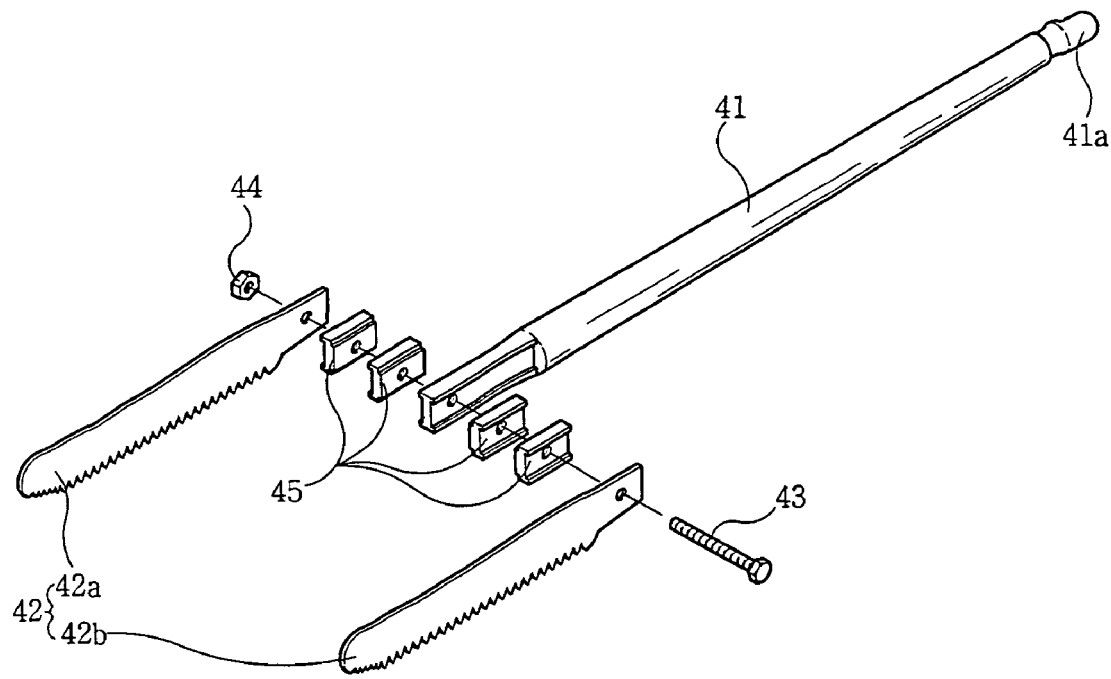
FIG. 7 is an exploded perspective view for a surgical saw for cutting off cheek bones according to another embodiment of the present invention.

Meanwhile, FIG. 7 is an exploded perspective view for showing a surgical saw for cutting off cheek bones according to another embodiment of the present invention.

Figure 8:
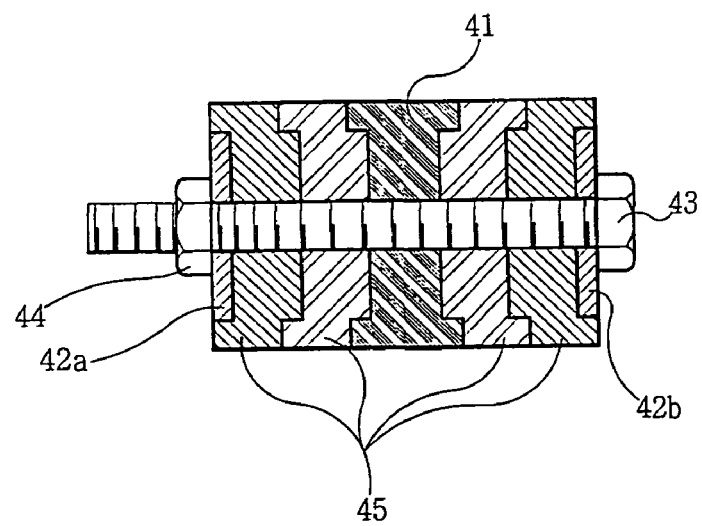
FIG. 8 is a cross-sectioned view taken along line VIII-VIII of FIG. 7.

As shown in FIG. 7, a surgical saw 40 for cutting off cheek bones according to another embodiment of the present invention includes a structure that individual separated saw blades of a double saw blade part 42 are fixed to the front end portion of an arm 41 by a fixing unit constructed with a bolt 43 and a nut 44. In particular, plural spacing members 45, for example, zero to four spacing members, can be selectively placed on both sides of the front end portion of the arm 41 and between individual saw blades 42a and 42b, and the members 45 and the blades 42a and 42b are tightly fixed to the arm 41 by the bolt and nut 43 and 44. Further, as shown in FIGS. 7 and 8, structures for preventing up-and-down movements are formed on the left and right sides of each of spacing members 45 as well as of the front end portion of the arm 31, having convex and concave portions to be matched with each other to restrain the individual saw blades 42a and 42b from relative movements in up and down directions among the constituents of the structure as well as movements of the individual saw blades 42a and 42b in up and down directions after the individual saw blades 42a and 42b are fixed to the front end portion of the arm with the spacing members 45 placed between the blades 42a and 42b and the front end portion.

With the structure mentioned above, in case that the surgical saw 40 for cutting off cheek bones according to another embodiment of the present invention is used in surgeries for cutting off cheek bones 101, the two saw blades 42a and 42b of the double saw blade part 42 can saw two positions of the cheek bones 101 at the same time so that a portion of the cheek bones 101 can be cut off through a one-time cutting operation. In particular, since the distance between the two saw blades 42a and 42b of the double saw blade part 42 can be adjusted by adding the spacing members 45, the surgical saw 40 has an advantage in that widths of cheek bones to be cut off can be diversely adjusted.

The surgical saws for cutting off cheek bones according to the present invention as stated above in detail carry out linear reciprocation movements by the handle or the motor built in the handle. In case that the saws are used in surgeries for cutting off cheek bones, the interval between the saw blades can be adjusted in advance and both saw blades of the combined double saw blades can cut two positions of the cheek bones at the same time in a precise cutting-off length so that the surgical saws can precisely cut off a portion of the cheek bones by a predetermined cutting-off width with a one-time cutting operation. Accordingly, when the surgical saws for cutting off cheek bones according to the present invention are used for surgeries for cutting off cheek bones, the surgeries for cutting off portions of cheek bones can be very conveniently carried out as well as the periods of time for the plastic surgeries for cheek bones can be greatly reduced. In addition, since portions of both cheek bones can be precisely cut off by a width set in advance, an occurrence frequency of asymmetric aftereffects of the left and right sides of a face due to different cutting-off widths of the left and right cheek bones upon plastic surgeries of the cheek bones can be drastically reduced.

What is claimed is:

1. A surgical saw for cutting off cheek bones, comprising:
an arm for mounting a rear end portion thereof in a jaw of a handle; and
a double saw blade connected with a front end portion of the arm and having two saw blades arranged side by side at a certain distance,
wherein the saw blades are respectively fixed on opposite sides of the front end portion of the arm by a fixing means,
wherein spacing members have left and right sides, at least one of the spacing members being placed between each of the saw blades and the front end portion of the arm for enabling the distance of the saw blades to be adjusted, and
wherein left and right sides of the spacing members and the front end portion of the arm have up-and-down movement preventing structures for preventing the saw blades from relative rotations with respect to the arm and each other wherein the up-and-down movement preventing structures comprise concaved sides of the spacing members and front end portion of the arm.

2. The surgical saw as claimed in claim 1, wherein the fixing means includes a bolt transversely penetrating the individual saw blades and the front end portion of the arm and a nut engaged with the bolt.

3. A surgical saw for cutting off cheek bones, comprising:
an arm fixed by mounting a rear end portion thereof in a jaw of a handle and having a pair of a concaved sides in a front end portion;
a double saw blade part connected with each of the concaved sides of the front end portion of the arm and having two saw blades arranged side by side in a certain distance; and
a plurality of spacing members having left and right sides, one of the sides of each spacing members having a concaved side for receiving the spacing members to be mounted side by side,
wherein the saw blades are respectively fixed with the spacing members on opposite sides of the front end portion of the arm by a fixing means,
wherein at least one of the spacing members being mounted in the concaved side in a front end portion and placed between each of the saw blades and the front end portion of the arm for enabling the distance of the saw blades to be adjusted in the concaved side of the spacing member, and
wherein left and right sides of the spacing members and the front end portion of the arm have up-and-down movement preventing structures for preventing the saw blades from relative rotations with respect to the arm and each other.

* * * * *